United States Patent [19]

Gordon

[11] 4,179,338

[45] Dec. 18, 1979

[54] MICROBIOLOGICAL MEDIUM SUITABLE FOR STERILIZATION BY IONIZING RADIATION

[76] Inventor: Maurice R. Gordon, 15 Stuyvesant Cir. W., South Setauket, N.Y. 11733

[21] Appl. No.: 900,791

[22] Filed: Apr. 27, 1978

Related U.S. Application Data

[63] Continuation-in-part of Ser. No. 834,169, Sep. 19, 1977, abandoned.

[51] Int. Cl.$^2$ .......................... C12K 1/00; C12K 1/10
[52] U.S. Cl. .................................. 435/243; 435/247; 435/173; 435/800; 426/240
[58] Field of Search ................. 195/100, 102, 103.5 M; 426/240

[56] References Cited

U.S. PATENT DOCUMENTS

| | | | |
|---|---|---|---|
| 2,832,689 | 4/1958 | Proctor et al. | 426/240 |
| 3,346,464 | 10/1967 | Ernst | 195/103.5 M |
| 3,415,718 | 12/1968 | Forkman et al. | 195/103.5 |
| 3,871,967 | 3/1975 | Abdou et al. | 195/100 |
| 3,935,067 | 1/1976 | Thayer | 195/100 X |
| 3,936,355 | 2/1976 | Lawson | 195/100 |
| 4,039,387 | 8/1977 | Simpson et al. | 195/100 |
| 4,071,412 | 1/1978 | Eisenberg et al. | 195/100 X |

*Primary Examiner*—David M. Naff
*Attorney, Agent, or Firm*—Brumbaugh, Graves, Donohue & Raymond

[57] ABSTRACT

A microbiological medium suitable for sterilization by ionizing radiation is prepared containing an electron acceptor that reduces adverse changes in the medium during ionizing radiation and increases the degree of ionization caused by ionizing radiation whereby a greater number of microorganisms is destroyed. A preferred electron acceptor is a combination of NADH and NAD or a combination of NADH and pyridoxine hydrochloride.

7 Claims, No Drawings

MICROBIOLOGICAL MEDIUM SUITABLE FOR STERILIZATION BY IONIZING RADIATION

This application is a continuation-in-part of co-pending application, Ser. No. 834,169 filed Sept. 19, 1977 now abandoned.

BACKGROUND OF THE INVENTION

This invention relates to microbiological media and to a method for sterilizing such media by ionizing radiation.

Microbiological media are artificial systems of chemicals and nutrients which are used to grow and culture microorganisms. The media can be liquid or solid and the composition varies widely depending on the specific microorganism to be cultured. Some of the standard media frequently used by microbiologists are: meat infusion, plant infusion, gelatin, meat hydrolyzate, potato, milk, sugar media, blood media, and other chemically defined media.

Before microbiological media can be used to grow microorganisms, the media must be sterilized. In its classical sense, the term sterilization is applied to techniques and processes by which materials are made free of any kind of life. sterilization is usually carried out by means of heat, radiation or physical removal of the contaminating organisms, for example, by filtration. Sterilization is approached as a probability function. In these terms, sterilization is a process by which the anticipated level of microbial contaminants in a material are exposed to a sterilant for the proper time so that the probability of an organism's surviving is $10^{-6}$. The time required to achieve a 90% kill through a log cycle is called the "D value".

Various types of sterilants are available for commercial use, for example, steam, gas, and radiation. The choice of a sterilant depends on the nature of the product to be sterilized, the effect of the sterilant upon the product, economic cost and the reliability of the sterilization procedure as based upon quality assurance tests. Steam under pressure is the most efficient sterilant. However, because of its high temperature, it cannot be used on many heat labile biochemical substances containing vitamins, amino acids, antibiotics, sugars, and alcohol additives.

Steam sterilization can cause detrimental hydrolysis of solid media by overheating which causes decreased gel strength due to damage to protein, or conversely can cause hardening of the media due to excessive water loss. The heat from steam sterilization can also cause a darkening of the media due to sugar carmelization and/or protein destruction, formation of precipitates, changes in pH and loss of growth promoting capacity.

If one or more of these heat sensitive substances are present in the substance to be sterilized, such as in microbiological media, the sterilization process must be broken into several steps whereby the heat sensitive portion of the media is sterilized by filtration and combined with the non-heat sensitive portions of the media which has been sterilized by steam. Such a procedure is time and energy consuming and raises the cost of preparing sterile microbiological media.

Sterilization through the use of ionizing radiation overcomes many of the problems found in steam sterilization since it destroys microorganisms in 0.5 to 1.5 seconds without a substantial rise in the temperature of the system and therefore offers an attractive means for sterilizing microbiological media as well as foods, drugs, and miscellaneous complex biochemical systems. U.S. Pat. Nos. 3,057,735 to Ottke, 2,992,927 to Radouco-Thomas and 2,832,689 to Proctor et al. are references which show some of these prior art uses of electron radiation as a means of sterilization.

It is believed that sterilization is accomplished by radiation primarily by ionization of chemical bonds, that is, the breaking of a molecule into a positive and negative portion. The heat released to the liquid portion of the media on ionization or the direct impact of the electron on the cell causes the destruction of the bacteria cell or mold thereby sterilizing the media. When destruction of the cell does not occur directly, the radiation causes genetic changes in the cell which prevent the cell from reproducing.

High energy electron beams appear to be the best source of ionizing radiation and in this form, it can be used in an efficient and controlled manner. Suitable sources include a high voltage source such as a Van de Graff generator or a linear accelerator. Accelerated electrons from these sources have energies in the region of 1-5 Mev and will penetrate to about a depth of 1 cm in an aqueous media. This is a drawback to this form of sterilization and several methods have been developed to increase the range of penetration of beams of electrons as disclosed in U.S. Pat. No. 2,897,365 to Dewey et al. Objects are irradiated from both sides by reversing the objects and irradiating them a second time or by irradiating the objects simultaneously with two electron sources. These methods are not practical or economically feasible for sterilizing media. Because the penetration of an electron beam is low, the ionizing activity in irradiated media is low and makes ionizing radiation an impractical means of industrial sterilization.

An additional problem associated with ionizing radiation sterilization is that most indicating dyes used in standard microbiological media are not suited for use in an ionizing radiation sterilization system. Standard indicating dyes can be affected by electrons directly, and indirectly by the ionization of the surrounding media which produces by-products that cause shifts in the pH of the media thereby affecting the color of the media. to indicate important chemical changes in the media, modifications must be made to media which are sterilized by ionizing radiation.

The present invention relates to improved microbiological media and a method for sterilizing them by ionizing radiation. Since it is believed that the number of microorganisms destroyed by radiation is directly related to the degree of ionization within the medium it is an object of the present invention to increase the destruction rate of the electron beam by the addition of electron acceptors to the medium which it is believed, will increase the degree of ionization and thereby the number of microorganisms destroyed.

It is a further object of this invention to prepare a medium which contains sufficient amounts of dye to withstand a sterilizing dose of ionizing radiation.

It is a further object of this invention to prepare a medium that has less water loss due to dessication during storage and less surface syneresis which thereby maintains excellent biochemical activity and reduces the chance of media contamination and deterioration.

It is a further object of this invention to prepare a sterile medium that has a shelf life of up to 2 years at room temperature thus decreasing cost of replacement of media and cold storage.

The foregoing and other objects, features and advantages of the invention will become more apparent from the following detailed description of the invention.

An improved microbiological medium has now been found, comprising a nutrient and an electron acceptor selected from the group consisting of:

β nicotinamide mononucleotide; β nicotinamide mononucleotide, reduced form, disodium; β nicotinamide adenine dinucleotide (NAD); β nicotinamide adenine dinucleotide, reduced form, disodium (NADH); nicotinamide adenine dinucleotide phosphate (NADP), nicotinamide adenine dinucleotide phosphate, reduced form (NADPH); α nicotinamide adenine dinucleotide (NAD); α nicotinamide adenine dinucleotide, reduced form, disodium (NADH); pyridoxine hydrochloride; pyridoxal-5-phosphate, HCl; p-phenylenediamine oxlate; cytochrome-C; and nicotinamide-1, $N^6$ etheno adenine dinucleotide phosphate, the electron acceptor being present at a level sufficient to allow the medium to be sterilized using ionizing radiation without adverse change in the medium.

It is preferable to use the coenzyme nicotinamide adenine dinucleotide in its reduced form, hereinafter sometimes referred to as NADH, in combination with unreduced nicotinamide adenine dinucleotide, hereinafter sometimes referred to as NAD, in its charged state as the electron acceptor. NAD is a coenzyme formed in the human body from nicotinic acid. The microbiochemical reactions of the coenzyme NAD are well known and have been studied extensively. Medicinal Chemistry, 3rd ed., Alfred Burger, page 804 and the references cited therein give detailed discussions of these reactions. Examples of these known reactions are the glycolysis pathway and tricarboxylic acid cycle.

The oxidation-reduction reaction of the NAD coenzyme is reversible and after aiding in the sterilization process, the coenzyme, as do all of the electron acceptors used in this invention, becomes an integral effective nutritive ingredient of the biological medium:

seconds in a 3vKV field using a 3MeV electron beam. The sterilized culture plates and tubes are stored at room temperature.

In an alternate form of the invention, NADH is used in combination with pyridoxine hydrochloride as an electron acceptor.

The presence of an electron acceptor such as $NAD^+$ and NADH or NADH and pyridoxine hydrochloride in microbiological media which is exposed to ionizing radiation, provides more effective sterilization than in media without the electron acceptors of the present invention. It is believed that this improved result is due to the fact that the presence of electron acceptors such as $NAD^+$ and NADH or NADH and pyridoxine hydrochloride in microbiological media enhances the ionization activity per unit volume of the media and thereby allows for destruction of a greater number of microorganisms. For example, NAD is an oxidizing agent which is reduced to NADH and NADH is a reducing agent which is oxidized to NAD. The $NAD^+$ in its charged state will remove hybrid ions $H^-$ from the media and will thereby be reduced to NADH and with the resulting production of a hydrogen ion $H^+$ which reacts further with incoming electrons. Since the oxidation reduction reaction is readily reversible, the NADH acts as a reducing agent and gives up electrons to ionize the substrate media to form free NAD. The free NAD initiates further oxidation reduction cycles and thereby continues to produce ionization and sterilization. In addition, the charged $NAD^+$ easily gains hydrogen ions to form neutral NAD. This reaction also increases the number of microorganisms destroyed and provides another source of oxidized NAD which further initiates oxidation reduction reaction and further ionization. This series of oxidation reduction reactions increases chemical activity within the media and the resulting ionization serves to enhance and disperse the sterilization effect of the electron beam throughout the media. In addition, the electron acceptors of this invention not

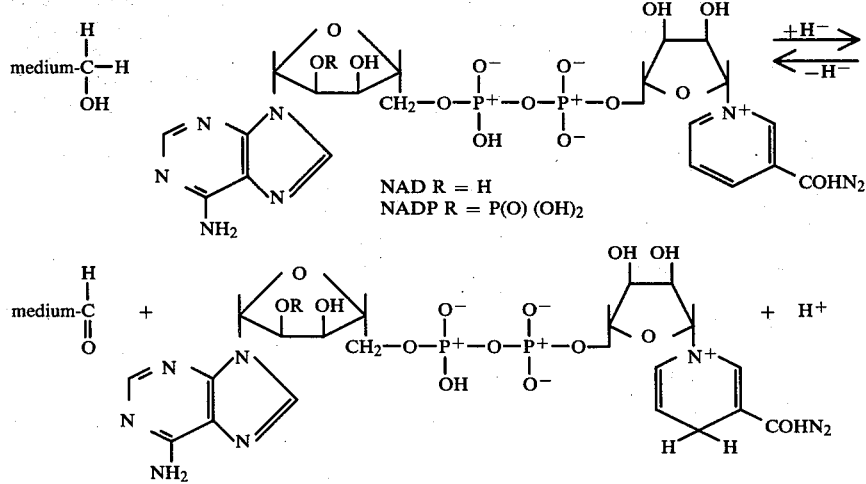

The medium is prepared in a phosphate buffer solution using standard microbiological ingredients. The electron acceptor is added to the medium at the same time as the nutritive ingredients of the medium are added. The finished medium is placed in suitable culture vessels such as petri dishes or culture tubes and are transported to a radiation source. The culture vessels are irradiated using a dose of 0.1–1.5 Mrads for 0.5–1.5 only serve to enhance ionization but also becomes part of the nutritive material in the media.

Because many of the indicating dyes used in the standard microbiological media are readily decolorized, that is, reduced by the electron beam, the composition of standard media may be modified by small increases in the weight of dye per volume of media, by adding a supplemental dye and/or by pre-reducing certain dyes.

These modifications are made so that the dye will be able to withstand a sterilizing dose of ionizing radiation.

The indicating dye is used in the media at a level which will be sufficient to withstand a sterilizing dose of ionizing radiation, that is, there will be sufficient dye remaining in the media after irradiation to act as an indicator. Basic Fushsin dye is normally used in microbiological media at a level of 0.8g/l. In order to compensate for the loss of dye due to irradiation, the amount of Basic Fuchsin normally used is increased up to a maximum of 1.6g/l. It is believed that the use of more than 1.6g/liter of Basic Fuchsin does not increase the ability of the media to withstand decolorization. Further examples of the modifications to the standard amount of dye used in media to be sterilized by ionizing radiation are listed in Table I.

TABLE I

| Indicating Dye | Amount of Dye Used In Standard Media | Maximum Amount of Dye Used In Media To Be Sterilized By Ionizing Radiation |
|---|---|---|
| Neutral Red | 0.03g/l | 0.06g/l |
| Crystal Violet | 0.001g/l | 0.0015g/l |
| Azide | 0.2g/l | 0.4g/l |
| Methylene Blue | 0.065g/l | 0.90g/l |
| Reduced Methylene Blue | 0.065g/l | 0.90g/l |
| Eosin Y | 0.4g/l | 0.8g/l |
| Brilliant Green | 0.0133g/l | 0.0266g/l |
| Brom Thymol Blue | 0.025g/l | 0.050g/l |
| Phenol Red | 0.08g/l | 0.16g/l |

In some cases a combination of dyes can be used. For example, Neutral Red can be used in combination with a dye selected from the group consisting of Eosin Y, Basic Thymol Blue, Crystal Violet and Basic Fuchsin. The total amount of the dye combination should not exceed 0.015g/l.

In order to improve and extend the shelf life of the media after irradiation, 1.2–2% by weight of glycerine is added to each batch of media before it is irradiated. The glycerine helps to retain fluids in solid media and also acts as a mild spore inhibitor. The glycerine aids in retaining the fluids within the solid types of media and helps to prevent surface syneresis, i.e., the separation of the liquid from the solid phase, and thus helps to eliminate surface contamination and thereby provide a longer shelf time of 24 months or more.

In addition to the longer shelf life, the media prepared according to this invention can be stored at room temperature and thus eliminates the need for long term refrigerated storage. This feature helps to save energy and thus lowers the cost of producing the media.

The following is a specific example of the invention but it is to be understood that it is by way of illustration and by no means limits the scope of this invention.

EXAMPLE 1

A phosphate buffer at pH 7.0 was prepared by dissolving 1.361 grams potassium dihydrogen phosphate ($KH_2PO_4$) and 1.420 grams anhydrous disodium hydrogen phosphate ($Na_2HPO_3$) in a two liter flask in 500 mls of boiled and cooled distilled water and diluted with 1,000 ml boiled and cooled distilled water. To the flask containing the buffer, 50 grams dry m-les-Endo agar were added and dissolved in the phosphate buffer at about 95° C. m-les-Endo agar was purchased from Baltimore Biological Laboratories and contained per 50 grams: 1.2g yeast extract, 3.7g trypticase peptone, 3.7g thiotone peptone, 7.5g biosate peptone, 9.4g lactose, 3.3g dipotassium phosphate, 1.0g monopotassium phosphate, 3.7g sodium chloride, 0.1g sodium desoxycholate, 0.05g sodium laurel sulfate, 1.6g sodium sulfite, 0.8 Basic Fuchsin and 14.08 dried agar. The solution was cooled to 65° C. and 0.4g Basic Fuchsin dye, U.S. certified grade, 1000 micrograms of NADH, 1000 micrograms of NAD+ and 12 grams of U.S.P. glycerine were dissolved. The NAD and NADH were purchased from Sigma Chemical Co. Culture plates were filled with the resulting solution to a depth of ¼ inch per plate and the plates were chilled to 2°–8° F. as rapidly as possible without causing the formation of ice crystals. The plates were transported to the radiation source and irradiated using a dose of 1.5 Mrads for 0.5 seconds in a 3v KV field using a 3MeV electron beam from an electron accelerator. The irradiated plates were stored in presterilized plastic bags and packed in cardboard boxes for storage at room temperature.

EXAMPLE 2

Culture tubes are prepared and sterilized exactly as in Example 1 except that standard culture tubes are filled to a level with the medium sufficient for culturing microorganisms.

EXAMPLE 3

A medium is prepared as in Example 1 except that NADH and pyridoxine hydrochloride are substituted for NAD+ and NADH.

EXAMPLE 4

A medium is prepared as in Example 1 using NADH and β nicotinamide mononucleotide in place of NAD+ and NADH.

EXAMPLE 5

A medium is prepared as in Example 1 using NADH and β nicotinamide mononucleotide, reduced form, disodium in place of NAD+ and NADH.

EXAMPLE 6

A medium is prepared as in Example 1 using NADH and pyridoxal-5-phosphate, HCl in place of NAD+ and NADH.

EXAMPLE 7

A medium is prepared as in Example 1 using NADH and nicotinamide adenine dinucleotide phosphate (NADP) in place of NAD+ and NADH.

EXAMPLE 8

A medium is prepared as in Example 1 using NADH and cytochrome-C in place of NAD+ and NADH.

EXAMPLE 9

A medium is prepared as in Example 1 using NADH and nicotinamide-1, $N^6$ etheno adenine dinucleotide phosphate in place of NAD+ and NADH.

It has been shown that any increase in the radiation level of the media due to the external source of radiation is only temporary and lasts only for several hours or less. There is no risk that this radiation might induce radioactivity in the treated media. Activation due to the electron beam is insignificant and when it does occur, the decay is rapid and complete.

When media containing blood cells from, for example, sheep, humans, horses or rabbits are sterilized by ionizing radiation, an extra step must be added to the preparation procedure. In order to prevent blood cells from decomposing during irradiation sterilization, the blood cells must be pretreated with a tanning agent such as tannic acid which adds strength to the cell wall by developing a strengthened protein coating.

EXAMPLE 10

2000 grams of concentrated sheep blood cells are added to 2 liters of a water solution buffered to pH 7.0 containing 0.5g tannic acid, 12g dextrose, 17g sodium chloride and 2g anhydrous sodium citrate and refrigerated for one week. After one week, the solution is gently decanted and replaced with 2 liters of a water solution buffered to pH 7 containing 0.2g tannic acid, 22g dextrose, 17g sodium chloride and 2g sodium citrate and refrigerated for an additional week. After a week, the second solution is gently decanted and replaced with 1 liter of a water solution buffered to pH 7 containing 0.2g tannic acid, 1.0 g sodium citrate, 8.5g sodium chloride and 15g dextrose. The treated sheep blood cell mixture is refrigerated and used within approximately twenty four hours to prepare blood media.

In a 1 liter volumetric flask, 40 grams of a dry peptone-casein digest medium purchased as Trypticase-Soy Agar from Baltimore Biological Laboratories were dissovled in the phosphate buffer described in Example 1 at about 95° C. The solution was cooled to 65° C. and 1000 micrograms of NADH, 1000 micrograms NAD+, 12 grams of U.S.P. glycerine and 50 ml of the tanned sheep blood cells described above were added and diluted to volume with phosphate buffer. The NADH and NAD were purchased from Sigma Chemical Co. Culture plates were filled with the resulting solution to a depth of ¼ inch per plate and the plates were chilled to 2°-8° F. as rapidly as possible without causing the formation of ice crystals. The plates were transported to the radiation source and irradiated using a dose of 1.5 Mrads for 0.5 second in a 3v KV field using 3MeV electron beam from an electron accelerator. The irradiated plates were stored in pre-sterilized plastic bags and packed in cardboard boxes for storage at room temperature. The sterile blood plates are stored at room temperature for at least 6 months.

I claim:

1. An improved microbiological medium suitable for sterilization by ionizing radiation comprising a buffer solution containing nutrients for microorganisms and an electron acceptor, the electron acceptor comprising $\alpha$ or $\beta$ nicotinamide adenine dinucleotide reduced form, disodium (NADH) in combination with a compound selected from the group consisting of $\beta$ nicotinamide mononucleotide; $\beta$ nicotinamide mononucleotide reduced form, disodium; $\alpha$ or $\beta$ nicotinamide adenine dinucleotide (NAD); pyridoxine hydrochloride; pyridoxal-5-phosphate, HCl; nicotinamide adenine dinucleotide phosphate (NADP); cytochrome-C and nicotinamide-1 $N^6$ etheno adenine dinucleotide phosphate, the electron acceptor being present at a level sufficient to allow the medium to be sterilized using ionization radiation without causing adverse change in the medium as compared to when no electron acceptor is present and at a sufficient level to increase the degree of ionization caused by ionizing radiation whereby the number of microorganisms destroyed during sterilization is increased as compared to when no electron acceptor is present.

2. An improved microbiological medium suitable for sterilization by ionizing radiation comprising a buffer solution containing nutrients for microorganisms, glycerine and an electron acceptor, the electron acceptor comprising $\alpha$ or $\beta$ nicotinamide adenine dinucleotide reduced form, disodium (NADH) and $\alpha$ or $\beta$ nicotinamide adenine dinucleotide (NAD), the electron acceptor being present at a level sufficient to allow the medium to be sterilized using ionizing radiation without causing adverse change in the medium as compared to when no electron acceptor is present and at a sufficient level to increase the degree of ionization caused by ionizing radiation whereby the number of microorganisms destroyed during sterilization is increased as compared to when no election acceptor is present.

3. An improved microbiological medium suitable for sterilization by ionizing radiation comprising a buffer solution containing nutrients for microorgaisms, glycerine and an electron acceptor, the electron acceptor comprising $\alpha$ or $\beta$ nicotinamide adenine dinucleotide reduced form, disodium (NADH) and pyridoxine hydrochloride, the electron acceptor being present at a level sufficient to allow the medium to be sterilized using ionizing radiation without causing adverse change in the medium as compared to when no electron acceptor is present and at a sufficient level to increase the degree of ionization caused by ionizing radiation whereby the number of microorganisms destroyed during sterilization is increased as compared to when no electron acceptor is present.

4. The microbiological medium as defined in claim 1, wherein the medium contains blood cells, the walls of which have been strengthened by pretreatment with a tanning agent.

5. The microbiological medium as defined in claim 4, wherein the tanning agent is tannic acid.

6. The microbiological medium as defined in claim 2, wherein the glycerine is used in the range of 1.2–2% by weight.

7. The microbiological medium as defined in claim 4, wherein the glycerine is used in the range of 1.2–2% by weight.

* * * * *

UNITED STATES PATENT AND TRADEMARK OFFICE
CERTIFICATE OF CORRECTION

PATENT NO. : 4,179,338
DATED : December 18, 1979
INVENTOR(S) : Maurice R. Gordon It is certified that error appears in the above-identified patent and that said Letters Patent are hereby corrected as shown below:

Col. 1, line 25, "sterilization" should be --Sterilization--;

Col. 8, line 30, "microorgaisms" should be --microorganisms--;

Col. 8, line 52, "claim 4" should be --claim 3--.

Signed and Sealed this

Third Day of June 1980

[SEAL]

Attest:

SIDNEY A. DIAMOND

Attesting Officer

Commissioner of Patents and Trademarks